United States Patent
Suzuki et al.

[11] Patent Number: 5,124,477
[45] Date of Patent: * Jun. 23, 1992

[54] PROCESS FOR PREPARING PARA-HYDROXYBENZOIC ACID

[75] Inventors: Toshinobu Suzuki; Makiko Ijiri; Hitoshi Saima; Tadahiro Wakui; Tokio Iizuka; Akinori Matsuura, all of Chiba, Japan

[73] Assignee: Kawasaki Steel Corporation, Hyogo, Japan

[*] Notice: The portion of the term of this patent subsequent to Dec. 10, 2008 has been disclaimed.

[21] Appl. No.: 448,333

[22] Filed: Dec. 11, 1989

[30] Foreign Application Priority Data

| Dec. 14, 1988 | [JP] | Japan | 63-315368 |
|---|---|---|---|
| Dec. 14, 1988 | [JP] | Japan | 63-315369 |
| Dec. 14, 1988 | [JP] | Japan | 63-315370 |
| Dec. 14, 1988 | [JP] | Japan | 63-315371 |
| Jan. 20, 1989 | [JP] | Japan | 1-12723 |
| Apr. 17, 1989 | [JP] | Japan | 1-96987 |
| Apr. 17, 1989 | [JP] | Japan | 1-96988 |
| Apr. 17, 1989 | [JP] | Japan | 1-96989 |
| Oct. 31, 1989 | [JP] | Japan | 1-283950 |

[51] Int. Cl.$^5$ .................................. C07C 51/15
[52] U.S. Cl. ...................................... 562/424
[58] Field of Search ................................ 562/424

[56] References Cited

U.S. PATENT DOCUMENTS

| 4,032,555 | 6/1977 | Bottaccio et al. | 260/465 D |
|---|---|---|---|
| 4,034,006 | 7/1977 | Lind et al. | 562/424 |
| 4,508,920 | 4/1985 | Stopp et al. | 562/424 |
| 4,529,817 | 7/1985 | Stopp et al. | 562/424 |

FOREIGN PATENT DOCUMENTS

| 0102833 | 3/1984 | European Pat. Off. |
|---|---|---|
| 61-115053 | 2/1986 | Japan . |
| 738359 | 10/1953 | United Kingdom . |

OTHER PUBLICATIONS

European Search Report for Appln. No. 89123037.7.
Patent Abstracts of Japan, vol. 10, No. 303 (C-378) [2359], Oct. 16, 1986.

Primary Examiner—Paul J. Killos
Attorney, Agent, or Firm—Oliff & Berridge

[57] ABSTRACT

The improved process for preparing para-hydroxybenzoic acid comprises reacting potassium phenol with carbon dioxide in an inert reaction medium or without using a reaction medium in the presence of at least one compound selected from the group consisting of the compounds represented by the following general formula I or II:

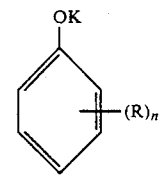

I

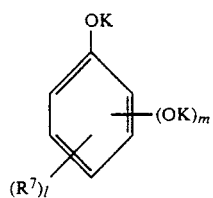

II at a reaction temperature of 230°–450° C. and at a carbon dioxide pressure ranging from atmospheric pressure to 6 kg/cm$^2$ (G). The process may comprise two stages and the first-stage reaction described above is followed by the second stage in which the reaction is further continued with the pressure of carbon dioxide in the system being reduced and/or the reaction temperature being elevated within the range specified above.

Also, phenol may be used as the starting material instead of potassium phenolate.

28 Claims, No Drawings

PROCESS FOR PREPARING PARA-HYDROXYBENZOIC ACID

BACKGROUND OF THE INVENTION

1. Field of the Invention

The present invention relates to a process for preparing para-hydroxybenzoic acid, in particular, a process by which para-hydroxybenzoic acid can be obtained not only in high yield but also in high selectivity since the generation of by-product salicylic acid can be suppressed.

2. Prior Art and Problems

Para-hydroxybenzoic acid finds a wide variety of applications as starting material for polymeric materials. Particularly in these days, it draws attention as starting material for liquid crystalline polyesters having high strength and high heat resistance. Also alkyl esters of para-hydroxybenzoic acid are useful as antimolds of cosmetics and industrial materials.

Para-hydroxybenzoic acid is basically produced by reacting an alkali salt of phenol with carbon dioxide. The processes for producing para-hydroxybenzoic acid are roughly divided into the Kolbe-Schmitt process in which the reaction between an alkali salt of phenol and carbon dioxide is carried out at elevated temperatures and pressures, and the Kolbe process in which the same reaction is performed at elevated temperatures under atmospheric pressure. It has been known for many years that whichever process is adopted, salicylic acid is generated as the main product if sodium phenolate is used as the starting material whereas para-hydroxybenzoic acid is generated if potassium phenolate is used.

The Kolbe-process involving reaction at atmospheric pressure has several advantages over the Kolbe-Schmitt process employing superatmospheric pressure, such as simplicity of apparatus, low equipment cost, ease of operations and control, and adaptability to continuous reaction. Nevertheless, the Kolbe-Schmitt process in which the reaction is carried out at elevated temperatures and pressures is currently used to produce para-hydroxybenzoic acid on an industrial scale, because the product yield by the Kolbe-Schmitt process is superior to that by the Kolbe process in which the same reaction is performed at elevated temperatures under atmospheric pressure.

Even by the Kolbe-Schmitt process, only about 50% of the yield can be achieved in most cases of the production of para-hydroxybenzoic acid, while a high yield of around 90% can be obtained in the case of the production of salicylic acid.

Recent studies on the Kolbe-Schmitt process have revealed that in the solid-gas phase reaction, not only is the efficiency of stirring operations low but also carbon dioxide is prevented from making effective contact with potassium phenolate. Further, heat transfer tends to become nonuniform, causing such shortcomings as the generation of by-product salicylic acid in increased amounts and the prolonged reaction time which takes as many as 4-7 hours. The by-product salicylic acid is an isomer of the desired para-hydroxybenzoic acid, the two compounds are similar in solubility and other physical properties. Hence, as the amount of the by-product salicylic acid generated increases, it becomes increasingly difficult to achieve efficient separation from para-hydroxybenzoic acid without reducing the purity and yield of the latter. All of these phenomena are deleterious in that the para-hydroxybenzoic acid obtained is not suitable for use in its intended applications.

With a view to eliminating the above-described shortcomings of the solid-gas phase reaction involved in the Kolbe-Schmitt process, the use of various inert reaction media has been proposed, as described in many patents including for example, Japanese Patent Publication No. 26612/1968, Japanese Patent Application Kokai No. 164751/1984, Japanese Patent Publication No. 9453/1971, etc. The method described in Japanese Patent Publication No. 9453/1971 is characterized by performing reaction in an aprotic polar solvent in the presence of an alkali metal or an alcoholate thereof. The yield of the para-hydroxybenzoic acid that can be obtained by this method is as high as 94% but at the same time, the amount of salicylic acid generated as a by-product is no smaller than 6%. In addition, alkali metals are not only expensive but also very hazardous since they will combine with water or methanol in an explosive way. Hence, alkali metals are not suitable for use in large-scale production. Even if one chooses to use alcoholates of alkali metals, they must be synthesized from alkali metals and alcohols, thus involving the same shortcomings as in the case using of alkali metals. Further, the lower alcohols that form as by-products will inhibit the progress of reaction and this necessitates performing the reaction with such alcohols being removed from the system.

Inert reaction media other than alkali metals and alcoholates thereof are also used in the prior art and it has been reported that the amount of salicylic acid generated as a by-product is a little less than 8% on the higher-content side and ranges from "not detected" to a little less than 2% on the lower-content side. However, even with these conventional methods, the yield of para-hydroxybenzoic acid that can be attained is generally about 50% and the exceptionally good result that has ever been reported is 77.3% (as described in Japanese Patent Application Kokai No. 164751/1984). Thus, up to the present day, there have been no processes in the art by which para-hydroxybenzoic acid can be produced at higher yields while the generation of the by-product salicylic acid can be suppressed to lower levels.

Prior to the application for this patent, the inventors of the present invention have applied for a patent (PCT/JP88/01051) with regard to a process for producing para-hydroxybenzoic acid in high yield by reacting an alkali phenolate with carbon dioxide in the presence of a substituted alkali phenolate (alkali metal; potassium, rubidium or cesium). In this prior application, however, a subject for repressing by-production of salicylic acid (that is, improvement of selectivity for the production of para-hydroxybenzoic acid) was remained unsolved. Therefore, the present inventors have performed detailed studies using potassium as an easily available alkali metal in order to solve this problem and have achieved the present invention.

It is, therefore, an object of the present invention to provide a process by which para-hydroxybenzoic acid having utility in a broad range of applications as the starting material for the production of various polymeric materials can be prepared not only in high yield but also with high selectivity and purity since the generation of the by-product salicylic acid can be suppressed to a lower level.

SUMMARY OF THE INVENTION

According to the process of the present invention, para-hydroxybenzoic acid can be obtained in a high yield which is at least 60%, preferably at least 80% and yet it can be produced with high selectivity and purity on account of the substantial absence of salicylic acid generated as a by-product. Hence, the para-hydroxybenzoic acid produced by the present invention finds utility in a very wide range of applications as a starting material for the manufacture of polymeric materials, pharmaceuticals and agrichemicals.

According to a first embodiment of the present invention, there is provided a process for preparing para-hydroxybenzoic acid which comprises reacting potassium phenolate with carbon dioxide in an inert reaction medium or without using a reaction medium in the presence of at least one compound selected from the group consisting of the compounds represented by the following general formula I or II:

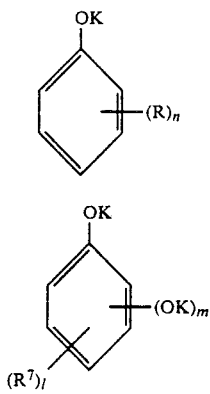

(in formula I, R may be any substituent except an aliphatic hydroxyl radical having up to 4 carbon atoms, an aliphatic mercapto radical having up to 4 carbon atoms, a substituent containing at least one of these radicals in its structural unit, and a hydrogen atom; in formula II, R' may be any substituent except an aliphatic hydroxyl radical having up to 4 carbon atoms, an aliphatic mercapto radical having up to 4 carbon atoms, and a substituent containing at least one of these radicals in its structural unit; in formula I, n is an integer of 1–5, provided that substituents R may be the same or different when n is 2 or more; and in formula II, m is an integer of 1–5 and ( is an integer of 0–4, provided that substituents R' may be the same or different when l is 2 or more) at a reaction temperature of 230°–450° C. and at a carbon dioxide pressure ranging from atmospheric pressure to 6 kg/cm² (G).

According to a second embodiment of the present invention, there is provided a two-stage process for preparing para-hydroxybenzoic acid, in which reaction is performed at the first stage in the manner described above, and at the subsequent second stage, the reaction is further continued with the pressure of carbon dioxide in the system being reduced and/or the reaction temperature being elevated within the range specified above.

In the first and second embodiments of the present invention, if at least either of (A) a mixed melting point of a mixture containing a potassium phenolate and at least one compound selected from the group consisting of the compounds represented by the general formula I or II and (B) the highest decarboxylation temperature of substituted potassium salicylates which are derived by ortho-carboxylation from a compound which is represented by the general formula I or II and has at least one hydrogen atom on the ortho position of the associated potassium oxy radical is within the range from 230° C. to 450° C., the reaction temperature is preferably within the range from the higher temperature selected from the mixed melting point or the decarboxylation temperature to 450° C.

It is preferred the potassium phenolate and the compounds represented by said formula I or II are derived from tar acids and/or cresol acids, the reaction of the potassium phenolate with carbon dioxide is performed in a flow or a circulation of carbon dioxide or carbon dioxide gas mixture containing formed phenol, with part or all of the resulting compounds represented by the following formulas III and/or IV being recovered or not recovered from the reaction system:

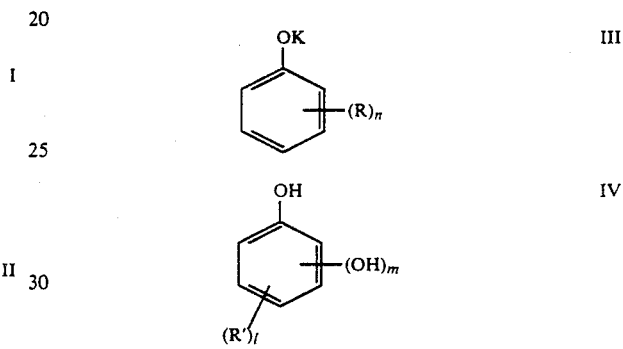

Also, the above-described flow or circulation of carbon dioxide or carbon dioxide gas mixture may be performed while phenol is added.

According to a third embodiment of the present invention, there is provided a process for preparing para-hydroxybenzoic acid wherein the reaction of carbon dioxide and a mixture of phenol (as a stating material instead of potassium phenolate) and at least one compound of the compounds represented by the general formula I or II is performed in an inert reaction medium or without using a reaction medium at a reaction temperature of 230°–450° C. and at a carbon dioxide pressure ranging from atmospheric pressure to 6 kg/cm² (G).

DETAILED DESCRIPTION OF THE INVENTION

Formula (I) representing the compound used herein is shown below.

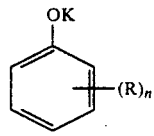

In formula (I), R is any substituent except an aliphatic hydroxyl radical having up to 4 carbon atoms, an aliphatic mercapto radical having up to 4 carbon atoms, a substituent having at least one of these radicals in its structural unit, and a hydrogen atom. Examples of the substituent represented by R include alkyl radicals, alkenyl radicals, alkynyl radicals, alkoxy radicals, amino radicals, imino radicals, halogen atoms, (aromatic) hydroxyl radicals, nitro radicals and phenyl radicals. These radicals may be substituted ones or a mixture of such radicals insofar as the above-mentioned requirement on R is met. Their examples include an isopropyl radical, aminoalkyl radical, alkylaminoalkyl radical, dialkylaminoalkyl radical, acylamino radical, halogenated alkyl radical, nitroalkyl radical, phenylalkyl radical, methoxy radical, alkylamino radical, dialkylamino radical, acyl radical, styryl radical, alkylphenyl radical, alkoxyphenyl radical, aminophenyl radical, halogenated phenyl radical, hydroxyphenyl radical, and nitrophenyl radical.

Preferred substituents R in formula I are electron donative radicals, for example, alkyl radicals such as methyl and alkoxy radicals such as methoxy although phenyl and similar radicals are also preferred.

Preferred compounds of formula I are potassium mono-substituted phenolates, in which the substituent may be at an ortho, meta or para position, with illustrative examples including potassium cresolate and potassium phenylphenolate (a potassium salt of hydroxybiphenyl).

Preferred compounds of formula I are potassium di-substituted phenolates, in which the two substituent positions may be in any combination, with illustrative examples including potassium 2,3-, 2,4-., 2,5-, 2,6-, 3,4- and 3,5-xylenolates.

Preferred compounds of formula I are potassium tri-substituted phenolates, in which the three substituent positions may be in any combination, and illustrative examples include potassium 2,4,6-, 2,3,4-, 2,3,5-, 2,3,6-, 2,4,5-, and 3,4,5-trimethylphenolates.

If a substituted potassium phenolate having a substituent at least on 2,4 and 6 positions is used as the compound of formula I in the practice of the present invention, the supply of potassium can be greatly facilitated since unlike other substituted potassium phenolates, this substituted form of potassium phenolate is of itself inert to carboxylation.

Formula II representing the compound used herein is shown below.

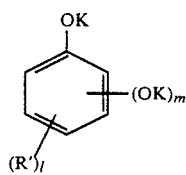

In formula II, R' includes those radicals defined for R and a hydrogen atom.

Preferred substituents in formula II are electron donative radicals, for example, alkyl radicals such as methyl and alkoxy radicals such as methoxy although a hydrogen atom, phenyl and similar radicals are also preferred.

Examples of the compounds represented by formula II include a dipotassium salt of dihydroxybenzene, as well as various other salts.

In the practice of the present invention, potassium phenolate and the compounds of formula I and/or II may be prepared from tar acids and/or cresol acids which are the mixtures of phenol and substituted phenols that are obtained from coal tar or the like. Such tar acids and cresol acids are inexpensive and form the mixture system contemplated herein, so they are particularly suited for the process of the present invention. Such tar acids or cresol acids, if used at all, may preferably be converted into potassium salts. In this case, illustrative compounds represented by formula I are potassium-cresolates, potassium-xylenolates, etc.

A reaction method using an inert reaction medium may be applied to the process of the present invention, and para-hydroxybenzoic acid can be obtained in high yield even without using a reaction medium. In particular, if the reaction temperature is above the mixed melting point of the mixture of raw materials, this mixture used as the starting material in the process of the present invention will become liquid on account of melting point depression. Thus, the mixture can be stirred more efficiently than in the conventional solid-gas phase reaction system even if no reaction media are used. Further, as the reaction proceeds, the compound of formulas I and/or II will be converted to a corresponding substituted phenol which is either a liquid or low-melting point compound, thus enabling the desired para-hydroxybenzoic acid to be obtained in a high yield.

Therefore, the melting point of the reaction mixture may be used as a marker to decide whether a reaction medium be introduced or not.

In the practice of the present invention, compounds represented by formula I or II may be used either on their own or as admixtures.

The amount of the compound of formula I and/or II that is contained in the reaction system may range from 0.2 to 30 equivalents, preferably from 0.5 to 10 equivalents, more preferably from 0.8 to 3 equivalents, as calculated in terms of the equivalent of the potassium oxy radical in these compounds based on the equivalent of the starting potassium phenolate. When a dipotassium salt of dihydroxybenzene is used as the compounds of formula II, its amount may range from 0.1 to 15 moles, preferably from 0.25 to 5 moles, more preferably from 0.4 to 1.5 moles, per mole of potassium phenolate.

This amount of the compound in the reaction system may be determined with considering about the melting point of this reaction mixture, preferably in the reaction system without solvent.

If the total amount of the mixed system of potassium phenolate and the compound represented by formula I and/or II is outside the range set forth hereinabove as calculated in terms of the equivalent of the potassium oxy radicals in these compounds, the amounts of the individual components, i.e., the compounds of formulas I and/or II and/or potassium phenolate, may be adjusted in such a way that their total amount will lie within the specified range. This adjustment procedure may be effected with the individual components being in the form of potassium salt described above. Alternatively, free acids of the respective components which are present in either excessive or insufficient amounts may be properly adjusted and thereafter converted to the corresponding potassium salts. If desired, the two adjusting methods may be combined.

In the process of the present invention, potassium phenolate is reacted with carbon dioxide in the presence of the compound of formula I and/or II at a reaction temperature of 230°–450° C. and at a carbon dioxide pressure ranging from atmospheric pressure to 6 kg/cm$^2$(G).

The lower limit of the reaction temperature that can be used in the process of the present invention is 230° C. because potassium salicylate which forms as a by-product and/or a reaction intermediate starts to decompose at about 232° C., peaking at about 246° C., and because above 230° C. either decarboxylation occurs or the condition favors rearrangement to potassium para-hydroxybenzoate. The upper limit of the reaction temperature is 450° C. because dipotassium para-hydroxybenzoate which forms predominantly when the potassium para-hydroxybenzoate generated by rearrangement or some other mechanism combines with the potassium originating from the compound of formula I and/or II is thermally stable up to about 454° C.

Thus, the preferred examples of the compound I and/or II that is to be contained in the reaction system of the present invention are such that the free acids that are derived from these compounds and which are represented by the following general formula III or IV:

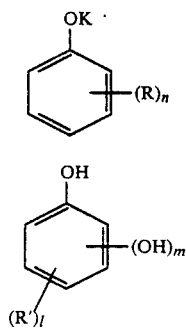

(In formula III, R and n are each the same as defined for formula I; and in formula IV, R', m and l are each the same as defined for formula II) have greater pKa values than that of the hydroxyl radical in para-hydroxybenzoic acid (pKa = 9.23). In other words, compounds having electron donative substituents are preferred since they provide a favorable condition for potassium transfer when highly heat-stable dipotassium para-hydroxybenzoate is being formed. The pKa value may therefore be used as a guide for selecting suitable compounds I and/or II in the practice of the present invention.

If the highest decarboxylation temperature of substituted potassium salicylates which are derived by ortho-carboxylation from a compound which is represented by the general formula I or II and has at least one hydrogen atom on the ortho position of the associated potassium oxy radical is within the range from 230° C. to 450° C., the reaction involved in the process of the present invention is preferably performed at a temperature ranging from said decarboxylation temperature to 450° C.

The reason for such a limitation is that some of these compounds I and/or II, in which the ortho position of the potassium oxy radical is carboxylated during the reaction, are decarboxylated at a temperature equivalent to or higher than their decarboxylation temperatures and reverted to the compound I and/or II itself and/or to the corresponding free acid represented by formula III or IV.

In fact, a potassium salt of these ortho-carboxylated compounds (substituted salicylic acids) resists rearrangement of the carboxyl radical to the para position, probably due to the steric hindrance by the substituent of interest and the reaction product have contained no detectable amount of a para-carboxyl compound that originates from the compound I and/or II.

By carrying out the reaction involved in the process of the present invention at a temperature ranging from the decarboxylation temperature of the substituted potassium salicylate to 450° C., not only salicylic acid but also the substituted salicylic acid compounds described above can be prevented from forming as by-products.

Take as an example the case where para-hydroxybenzoic acid is produced by the process of the present invention with potassium para-cresylate being used as compound I. Since potassium 2,5-cresotinate which is the product of ortho-carboxylation of this compound has a decarboxylation temperature of 279° C. (peak value), not only salicylic acid but also 2,5-cresotinic acid can be prevented from forming as by-products by performing the reaction under consideration at 279°–450° C. To mention the decarboxylation temperatures of other species of potassium cresotinate, potassium 2,3-cresotinate and potassium 2,4-cresotinate decarboxylate at 266° C. and 274° C., respectively.

The above discussion leads to the conclusion that if the compound I and/or II has a hydrogen atom on the ortho position of the potassium oxy radical, it is preferably such that the derived potassium salt of orthocarboxyl compound (i.e., substituted salicylic acid) has a low, rather than high, decarboxylation temperature.

A patent has already issued on a technique by which a substituted alkali phenolate corresponding to the compound I and/or II is independently reacted with carbon dioxide to have it derived to a carboxylated form (EP-0102833). However, the present invention is not obvious from this patent since it relates to a process in which the mixture of potassium phenolate and the compound I and/or II is reacted with carbon dioxide so that the generation of salicylic acid compounds which are carboxylated compounds derived from the compound I and/or II is suppressed and yet the desired para-hydroxybenzoic acid is obtained in high yield with high selectivity.

As described above, suitable examples of compound I and/or II may be selected in consideration of the pKa values of the corresponding free acids (compounds represented by formula III or IV). If these compounds have such a nature they will undergo ortho-carboxylation, not only their pKa values but also the decarboxylation temperatures of the corresponding potassium ortho-carboxylates may be used as guides.

Regarding the reaction temperature, it is preferable that the temperature is equivalent to or higher than the decarboxylation temperature, more preferably equivalent to or higher than the mixed melting point.

The carbon dioxide pressure to be used in the process of the present invention ranges from atmospheric pressure to 6 kg/cm$^2$(G). This is because decarboxylation of the by-product potassium salicylate and/or substituted potassium salicylate favors lower pressures and because in order to introduce carbon dioxide on the para position of potassium phenolate, it is advantageous to apply pressures of up to 6 kg/cm$^2$(G). If the carbon dioxide pressure is raised to an extreme level, not only does it become difficult to suppress the formation of salicylic acid and/or substituted salicylic acid compounds but also the carboxylation will proceed further to generate 4-hydroxyisophthalic acid as an additional by-product. The amount of this additionally formed by-product has a tendency to increase with increasing carbon dioxide pressure.

Hence, a reasonably high reaction temperature is preferably combined with a reasonably low carbon dioxide pressure within the ranges specified herein.

The carbon dioxide to be used in the present invention may be diluted or mixed with gases which are inert to the starting materials and the product under the reaction conditions specified herein. For example, carbon dioxide may be introduced in admixture with nitrogen, hydrogen, helium, argon, carbon monoxide, hydrocarbons, phenols and the like. Blast furnace gases resulting from ironmaking plants as by-products and emissions produced from industrial combustion processes also contain carbon dioxide and may be used with an economic advantage. When such carbon dioxide gas mixtures are used, the reaction involved in the process of the present invention may be performed with the carbon dioxide partial pressure adjusted to be within the range from atmospheric pressure to 6 kg/cm$^2$ (G).

In the practice of the process of the present invention, carbon dioxide or a carbon dioxide gas mixture containing one or more of the inert gases mentioned above may be supplied into the system by means of such devices as a pump, a compressor and/or a blower and optionally circulated through the system to stir the reaction mixture or assist in its stirring.

When potassium phenolate is reacted with carbon dioxide in the presence of at least one compound selected from among the compounds represented by the general formula I or II in accordance with the present invention, it is preferred that carbon dioxide or carbon dioxide gas mixture containing formed phenol is flowed or recycled into or through the system with part or all of the resulting compounds of formula III and/or IV being recovered or not being recovered from the reaction system.

This approach has several advantages including improvement in the selectivity for para-hydroxybenzoic acid and the possibility of recycling the distilling free phenols for reuse in the reaction. A particular advantage will result if potassium salts of tar acids and/or cresylic acids are used as starting materials since cresylic acids, or mixtures of phenols and/or substituted phenols, which are useful as starting materials for the manufacture of bakelite or as solvents for electric wire coatings can be recovered simultaneously with the production of para-hydroxybenzoic acid. The process conditions of this approach may be suitably determined in consideration of the balance between the boiling point of the material to be recovered by distillation and the reaction temperature specified herein.

The process of the present invention may be carried out in either a batchwise or continuous manner or in a combined manner although continuous operation is preferred because of the industrial advantages it offers.

The process of the present invention may be carried out in an inert reaction medium or it may be performed without using any reaction media. When the process of the present invention is to be carried out in an inert reaction medium, examples of such medium include aromatic hydrocarbons, aromatic ethers, aromatic alkanes, aromatic alkenes, aromatic ketones, and hydrogenated products thereof, aliphatic petroleum hydrocarbons, aprotic polar solvents, and higher alcohols. These reaction media may be used alone or as a mixture of two or more. Illustrative examples include biphenyl, terphenyl, naphthalene, anthracene, ditolylethane, dibenzyltoluene, methylnaphthalene, isopropylnaphthalene, GS 250 (a mixture of aromatic compounds containing methylnaphthalene as a main ingredient), NeoSK oil (available from Soken Chemical K.K.), Dowtherm (a mixture of diphenyl and diphenylether), ethylbiphenyl, diphenyl ether, hydrogenated terphenyl, benzophenone, kerosene and/or gas oil having a boiling point of at least 150° C., N,N-dimethylformamide, N,N-dimethylacetamide, dimethylsulfoxide, hexamethylphosphoramide, higher alcohols having 5 to 15 carbon atoms, and mixtures thereof. Preferred are those media in which potassium phenolate and the substituted potassium phenolate of formula I and/or II are not soluble, which are insoluble in water, and which are liquid at a temperature of at least 100° C., more conveniently liquid at a temperature above room temperature, and more preferably have a boiling point of at least 200° C.

Illustrative examples are gas oil having a boiling point of at least 250° C., NeoSK-oil, Dowtherm, and isopropylnaphthalene. The use of these media has an additional advantage of providing ease of control of reaction pressure.

In order to carry out the reaction in a continuous manner in a reaction medium, the reaction medium may be selected by taking into account its melting point, fluidity and solubility of free phenols.

The reaction system may be agitated irrespective of whether the reaction medium is present or absent. High speed rotation and/or vigorous shaking is preferred to insure effective contact between the reactants, and conditions that produce turbulent flows are more preferred.

The potassium phenolate and the substituted potassium phenolate of formula I and/or II used herein are preferably in powder form. Smaller particle sizes are preferred for both compounds. The particle size is an important factor for the reaction to be performed in the absence of a reaction medium.

If it is necessary to further suppress the formation of salicylic acid and/or substituted salicylic acid compounds, the first-stage reaction which is performed within the temperature and carbon dioxide pressure ranges described herein-above to form stable dipotassium para-hydroxybenzoate may be follows by a post treatment in which the second-stage reaction is performed at a lower carbon dioxide pressure and/or at a temperature increased within the range of 230°–450° C.

An example of the post treatment is to perform decarboxylation of potassium salicylate and/or substituted potassium salicylate by purging part of carbon dioxide from a superatmospheric system to reduce the pressure in the system, or by replacing part of all of the carbon dioxide with another inert gas to reduce the carbon dioxide partial pressure, and if necessary, by further reducing the pressure in the system to a subatmospheric level. In this case, the phenol forming as a by-product and/or the free acids (compounds represented by formula III or IV) originating from the compounds I and/or II will easily distill off, so these materials can conveniently be recovered by distillation. A particular advantage will result if tar acids and/or cresol acids are used as starting materials since the recovered distillate has an added value as cresol acid and hence increases the process economy.

Thus, the two-stage process which is included in the scope of the present invention has the advantage that the compound I and/or II, and/or the unreacted potassium phenolate can be recovered on their own and/or as free acids for use in subsequent cycles of the reaciton.

In the process of the present invention, phenol can be added to carbon dioxide or carbon dioxide gas mixture to be flowed or circulated. In the reaction system, phenol is converted to potassium phenolate which is a starting material for the production of para-hydroxybenzoic acid, by the action of the co-existing compound as potassium source originating from the compound represented by the formula I or II.

In addition, in the process of the present invention, phenol can be used as a starting material instead of potassium phenolate for the production of para-hydroxybenzoic acid, by reacting phenol with carbon dioxide in an inert medium or without using reaction media in the presence of at least one compound selected from the compounds represented by formula I or II at a reaction temperature of 230° C. to 450° C. and at a carbon dioxide pressure ranging from atmospheric pressure to 6 kg/cm$^2$ (G).

The amount of the compound of formula I or II that is contained in the reaction system may range from 0.6 to 50 equivalents, preferably 1.0 to 10 equivalents, more preferably 1.6 to 5 equivalents, as calculated in terms of the equivalent of the potassiumoxy radical in these compounds based on the equivalent of the hydroxy radical in phenol as the starting material.

Other preferable conditions are similar to the case of potassium phenolate as the starting material.

EXAMPLES

Examples and comparative examples are given below to illustrate the present invention. In the following examples and comparative examples, quantitative determination was by chromatography.

COMPARATIVE EXAMPLE 1

A pressure vessel was charged with 6.62 g of potassium phenolate and 25 ml of NeoSK-1400 (a dibenzyltoluene mixture medium produced by Soken Chemical K.K. With stirring at 1,000 r.p.m., reaction was carried out at a carbon dioxide pressure of 8 kg/cm$^2$ (G) and 230° C. for one hour.

An analysis of the reaction product after conversion to acid form showed a para-hydroxybenzoic acid yield of 46.4% on the basis of the potassium phenolate, with 1.7% salicylic acid forming as a by-product.

COMPARATIVE EXAMPLE 2

A pressure vessel was charged with 6.68 g of potassium phenolate, 2.42 g of phenol and 25 ml of NeoSK-1400 and reaction was carried out under the same conditions as those employed in Comparative Example 1.

An analysis of the reaction product after conversion to acid form showed a para-hydroxybenzoic acid yield of 45.7% on the basis of the potassium phenolate, with 1.9% salicylic acid forming as a by-product.

COMPARATIVE EXAMPLE 3

A pressure vessel was charged with 6.98 g of potassium phenolate, 7.54 g of potassium meta cresolate and 25 g of NeoSK 1400. With stirring at 1,000 r.p.m., reaction was carried out at a carbon dioxide pressure of 7 kg/cm$^2$ (G) and at 300° C. for one hour. An analysis of the reaction mixture after conversion to acid form showed a para-hydroxybenzoic acid yield of 80.0% on the basis of potassium phenolate, with 3.6% salicylic acid forming as a by product.

EXAMPLE 1

A pressure vessel was charged with 6.64 g of potassium phenolate and 8.77 g of potassium 2,4,6-trimethylphenolate, both being in a dry powder form, and 25 ml of NeoSK-1400. With stirring at 1,000 r.p.m., reaction was carried out at a carbon dioxide pressure of 4 kg/cm$^2$ (G) and at 300° C. for one hour.

An analysis of the reaction product after conversion to acid form showed a para-hydroxybenzoic acid yield of 87.3% on the basis of potassium phenolate, with 0.1% salicylic acid forming as a by-product.

EXAMPLE 2

A pressure vessel was charged with 6.60 g of potassium phenolate and 8.80 g of potassium 2,4,6-trimethylphenolate, both being in a dry powder form, and 25 ml of NeoSK-1400. With stirring, reaction was carried out at a carbon dioxide pressure of 6 kg/cm$^2$ (G) and at 260° C. for 20 minutes.

An analysis of the reaction product after conversion to acid form showed a para-hydroxybenzoic acid yield of 85.8% on the basis of the potassium phenolate, with 0.2% salicylic acid forming as a by-product.

EXAMPLE 3

A pressure vessel was charged with 6.61 g of potassium phenolate and 8.76 g of potassium 2,4,6-trimethylphenolate, both being in a dry powder form. With stirring, reaction was carried out at a carbon dioxide pressure of 6 kg/cm$^2$ (G) and at 230°-250° C. for 20 minutes. The equimolar mixture of potassium phenolate and potassium 2,4,6-trimethylphenolate had a melting point of 228° C.

An analysis of the reaction product after conversion to acid form showed a para-hydroxybenzoic acid yield of 80.1% on the basis of the potassium phenolate, with 0.9% salicylic acid forming as a by-product.

EXAMPLE 4

A pressure vessel was charged with 6.61 g of potassium phenolate and 8.72 g of potassium 2,4,6-trimethylphenolate, both being in a dry powder form, and 25 ml of NeoSK-1400. With stirring, reaction was carried out at a carbon dioxide pressure of 3 kg/cm$^2$ (G) and at 250° C. for one hour. Thereafter, the pressure in the vessel was reduced to one atmosphere and with stirring at 1,000 r.p.m., the reaction was continued for another one hour at 300° C. with forced circulation of carbon dioxide.

An analysis of the reaction product after conversion to acid form showed a para-hydroxybenzoic acid yield of 86.1% on the basis of the potassium phenolate, but by-product salicylic acid was not detected at all.

EXAMPLE 5

A pressure vessel was charged with 6.70 g of potassium phenolate and 8.87 g of potassium 2,4,6-trimethylphenolate, both being in a dry powder form, and 25.2 g of NeoSK-1400. With stirring, reaction was carried out at a carbon dioxide pressure of 5 kg/cm$^2$ (G) and at 280° C. for one hour. Thereafter, the pressure in the vessel was reduced to one atmosphere and with stirring at 1,000 r.p.m., the reaction was continued for another 30 minutes at 280° C. in a nitrogen stream.

An analysis of the reaction product after conversion to acid form showed a para-hydroxybenzoic acid yield of 83.4% on the basis of the potassium phenolate, but by-product salicylic acid was not detected at all.

EXAMPLE 6

Tar acids, or mixture of phenols as obtained from coal tar, were used and a dry potassium salt of tar acids was prepared from said tar acids and potassium hydroxide.

This potassium salt was found to contain, on a weight basis, 40.96% potassium phenolate, 9.66% potassium ortho-cresolate, 17.82% potassium meta-cresolate, 9.23% potassium para-cresolate, and 9.19% potassium xylenolates. The residual content (13.14%) comprised impurities characteristic of tar acids such as thiophenols but details were unknown.

A pressure vessel was charged with 14.20 g of this potassium salt of the tar acids in powder form together with 25.6 g of NeoSK-1400. With stirring at 1,000 r.p.m., reaction was carried out at a carbon dioxide pressure of 3 kg/cm$^2$ (G) and at 300° C. for one hour.

An analysis of the reaction product after conversion to acid form showed a para-hydroxybenzoic acid yield of 86.0% on the basis of the potassium phenolate, with 0.8% salicylic acid forming as a by-product.

EXAMPLE 7

The same potassium salt of tar acids as used in Example 6 was charged in an amount of 14.05 g into a pressure vessel together with 25 ml of isopropylnaphthalene. With stirring, reaction was carried out at a carbon dioxide pressure of 5 kg/cm$^2$ (G) and at 280° C. for one hour.

An analysis of the reaction product after conversion to acid form showed a para-hydroxybenzoic acid yield of 83.1% on the basis of the potassium phenolate, with 1.1% salicylic acid forming as a by-product.

EXAMPLE 8

A pressure vessel was charged with 6.70 g of potassium phenolate and 7.59 g of potassium para-cresolate, both being in a dry powder form, and 25 ml of NeoSK-1400. With stirring, reaction was carried out at a carbon dioxide pressure of 5 kg/cm$^2$ (G) and at 300° C. for one hour.

An analysis of the reaction product after conversion to acid form showed a para-hydroxybenzoic acid yield of 91.2% on the basis of potassium phenolate, with 0.6% salicylic acid forming as a by-product.

EXAMPLE 9

A pressure vessel was charged with 6.70 g of potassium phenolate and 7.45 g of potassium meta-cresolate, both being in a dry powder form. With stirring, reaction was carried out at a carbon dioxide pressure of 5 kg/cm$^2$ (G) and at 250°-270° C. for one hour. The equimolar mixture of potassium phenolate and potassium meta-cresolate had a melting point of 243° C.

An analysis of the reaction product after conversion to acid form showed a para-hydroxybenzoic acid yield of 83.2%, with 0.8% salicylic acid forming as a by-product.

EXAMPLE 10

A pressure vessel was charged with 6.63 g of potassium phenolate and 7.41 g of potassium para-cresolate, both being in a dry powder form. With stirring, reaction was carried out at a carbon dioxide pressure of 6 kg/cm$^2$ (G) and at 240°-255° C. for 30 minutes. The equimolar mixture of potassium phenolate and potassium para-cresolate had a melting point of 229° C.

An analysis of the reaction product after conversion to acid form showed a para-hydroxybenzoic acid yield of 74.2%, with 1.4% salicylic acid forming as a by-product.

EXAMPLE 11

A pressure vessel was oharged with 6.62 g of potassium phenolate and 8.10 g of potassium 3,5-xylenolate, both being in a dry powder form. With stirring, reaction was performed at a carbon dioxide pressure of 5 kg/cm$^2$ (G) and at 280°-295° C. for one hour. The equimolar mixture of potassium phenolate and potassium 3,5-xylenolate had a melting point of 246° C.

An analysis of the reaction product after conversion to acid form showed a para-hydroxybenzoic acid yield of 86.8%, with 1.0% salicylic acid forming as a by-product.

EXAMPLE 12

A pressure vessel was charged with 6.6 g of potassium phenolate and 7.3 g of potassium ortho-cresolate, both being in a dry powder form, and 25 g of NeoSK-1400. With stirring, reaction was performed at a carbon dioxide pressure of 3 kg/cm$^2$ (G) and at 250° C. for one hour.

An analysis of the reaction product after conversion to acid form showed a para-hydroxybenzoic acid yield of 87.4%, with 0.6 salicylic acid forming as a by-product.

EXAMPLE 13

A pressure vessel was charged with 6.6 g of potassium phenolate and 7.4 g of potassium meta-cresolate, both being in a dry powder form, and 25 g of NeoSK-1400. With stirring, reaction was performed at a carbon dioxide pressure of 3 kg/cm$^2$ (G) and at 300° C. for one hour.

An analysis of the reaction product after conversion to acid form showed a para-hydroxybenzoic acid yield of 84.9%, with 0.6% salicylic acid forming as a by-product.

EXAMPLE 14

Cresol acids, or mixture of phenols as obtained by distilling the acids from coal tar, were used and dry potassium cresolate was prepared from said cresol acids and potassium hydroxide. This potassium cresolate was found to contain, on a weight basis, 44.59% potassium phenolate, 11.87% potassium ortho-cresolate, 28.07% potassium metacresolate, 14.14% potassium para-cresolate, and 1.30% potassium xylenolates.

A pressure vessel was charged with 14.04 g of this potassium cresolate in powder form together with 25 g of NeoSK-1400. With stirring at 1,000 r.p.m., reaction was performed at a carbon dioxide pressure of 5 kg/cm$^2$ (G) and at 280° C. for one hour.

An analysis of the reaction product after conversion to acid form showed a para-hydroxybenzoic acid yield of 89.9% on the basis of the potassium phenolate, with 0.8% salicylic acid forming as a by-product.

EXAMPLE 15

A pressure vessel was charged with 7.53 g of potassium 2,3,5-trimethylphenolate, 5.71 g of potassium phenolate and 25 g of NeoSK-1400. Reaction was performed at a carbon dioxide pressure of 3 kg/cm$^2$ (G) and at 260° C. for 10 minutes.

An analysis of the reaction product after conversion to acid form showed a para-hydroxybenzoic acid yield of 73.0% on the basis of the potassium phenolate, but by-product salicylic acid was not detected at all.

EXAMPLES 16 to 21

A pressure vessel was charged with 6.6 g of potassium phenolate and 8.0 g of potassium xylenolate, both being in a dry powder form, and 25 g of NeoSK-1400, and reaction was performed under the conditions described in Table 1. After the reaction, the products were converted to acid form and subjected to quantitative analyses. The yield of para-hydroxybenzoic acid on the basis of potassium phenolate and that of by-product salicylic acid are also shown in Table 1.

TABLE 1

| Example No. | Potassium xylenolate | Reaction temp. (°C.) | $CO_2$ pressure (kg/cm$^2$, G) | Reaction time (h.) | Yield of para-hydroxy-benzoic acid (%) | Yield of salicylic acid (%) |
|---|---|---|---|---|---|---|
| 16 | potassium 2,3-xylenolate | 280 | 5 | 1 | 91.8 | 0.2 |
| 17 | potassium 2,4-xylenolate | 290 | 5 | 1 | 92.1 | 1.2 |
| 18 | potassium 2,5-xylenolate | 310 | 6 | 1 | 83.8 | 0.1 |
| 19 | potassium 2,6-xylenolate | 300 | 2 | 1 | 90.6 | 1.2 |
| 20 | potassium 3,4-xylenolate | 300 | 3 | 1 | 89.4 | 0.4 |
| 21 | potassium 3,5-xylenolate | 270 | 4 | 1 | 82.1 | 1.0 |

EXAMPLE 22

A pressure vessel was charged with 10.98 g of potassium ortho-phenylphenolate, 6.60 g of potassium phenolate and 25 g of NeoSK-1400. With stirring at 1,000 r.p.m., reaction was performed at a carbon dioxide pressure of 5 kg/cm$^2$ (G) and at 300° C. for one hour.

An analysis of the reaction product after conversion to acid form showed a para-hydroxybenzoic acid yield of 79.3% on the basis of potassium phenolate, with 1.07% salicylic acid forming as a by-product.

EXAMPLE 23

The procedure of Example 22 was repeated under the same conditions except that 10.98 g of potassium ortho-phenylphenolate was replaced by 10.96 g of potassium metaphenylphenolate.

An analysis of the reaction product after conversion to acid form showed a para-hydroxybenzoic acid yield of 80.4% on the basis of the potassium phenolate, with 0.8% salicylic acid forming as a by-product.

EXAMPLE 24

A pressure vessel was charged with 6.64 g of potassium phenolate, 5.72 g of dipotassium pyrocatechol and 25 g of NeoSK-1400. With stirring, reaction was performed at a carbon dioxide pressure of 3 kg/cm$^2$ (G) and at 240° C. for one hour.

An analysis of the reaction product after conversion to acid form showed a para-hydroxybenzoic acid yield of 60.2% on the basis of the potassium phenolate, but by-product salicylic acid was not detected at all.

EXAMPLE 25

A pressure vessel was charged with 6.6 g of potassium phenolate and 7.4 g of potassium para-cresolate, both being in a dry powder form, and 25 g of NeoSK-1400. With stirring, reaction was performed at a carbon dioxide pressure of 4 kg/cm$^2$ (G) and at 300° C. for one hour. Thereafter, the pressure in the vessel was lowered to one atmosphere and the reaction was continued for an additional one hour with stirring at 300° C., with forced circulation of carbon dioxide through the system, to effect a post treatment while collecting the distillate.

An analysis of the reaction product after conversion to acid form showed a para-hydroxybenzoic acid yield of 78.6% on the basis of potassium phenolate, with by-product salicylic acid being 0.1%.

Formation of 2,5-cresotinic acid as a by product was 1.8% on the basis of potassium para-cresolate. Yields of phenol (on the basis of potassium phenolate) and para-cresolate (on the basis of potassium para-cresolate) in the reaction system were 8.4% and 20.5%, respectively. An analysis of the condensate showed the formation of 12.3% of phenol on the basis of potassium phenolate and 76.3% of paracresol on the basis of potassium para-cresolate. Other by products were not detected.

EXAMPLE 26

A separable glass flask was charged with 12.8 g of potassium salts of tar acids (41.6 mmol of potassium phenolate, 28.7 mmol of potassium cresolates and 8.8 mmol of potassium xylenolates) and 44.5 g of NeoSK-1400. With stirring at 500 r.p.m., carbon dioxide was injected and circulated at a flow rate of 100 cc/min and the temperature of the charge was raised to 300° C., which was subsequently maintained for one hour.

The vapor emission from the reaction system was cooled and condensed in the trap, but the produced phenol was recirculated together with carbon dioxide. The amount of the trapped cresol and xylenol were 52% and 40%, respectively.

An analysis of the reaction product after conversion to acid form showed a para-hydroxybenzoic acid yield of 71.5% on the basis of potassium phenolate, with only 0.5% salicylic acid forming as a by-product.

EXAMPLE 27

The procedure of Example 26 was repeated under the same conditions except that 14.1 g of potassium salts of tar acids (46.4 mmol of potassium phenolate, 33.7 mmol of potassium cresolates and 10.7 mmol of potassium xylenolates) and 43.6 g of NeoSK-1400 were used and that the reaction mixture was held at 300° C. for two hours.

An analysis of the reaction product after conversion to acid form showed a para-hydroxybenzoic acid yield of 77.2% on the basis of potassium phenolate, with 1.1% salicylic acid forming as a by-product.

EXAMPLE 28

The procedure of Example 26 was repeated under the same conditions except that 50.6 mmol of potassium phenolate, 50.3 mmol of potassium para-cresolate and 46.2 g of NeoSK-1400 were used and that carbon dioxide was blown from below the agitator blades.

An analysis of the reaction product after conversion to acid form showed a para-hydroxybenzoic acid yield of 72.0% on the basis of potassium phenolate, with 0.9% salicylic acid forming as a by-product.

EXAMPLE 29

The procedure of Example 26 was repeated under the same conditions except that 14.2 g of potassium salts of tar acids (48.8 mmol of potassium phenolate, 34.9 mmol of potassium cresolates and 8.9 mmol of potassium xylenolates) and 44.0 g of NeoSK-1400 were used and that carbon dioxide and nitrogen were injected at flow rates of 150 cc/min and 50 cc/min, respectively.

An analysis of the reaction product after conversion to acid form showed a para-hydroxybenzoic acid of 71.4% on the basis of potassium phenolate.

EXAMPLE 30

The procedure of Example 26 was repeated under the same conditions except that 28.0 g of potassium salts of tar acids (91.6 mmol of potassium phenolate, 62.4 mmol of potassium cresolates and 18.4 mmol of potassium xylenolates) and 44.3 g of NeoSK-1400 were used and that carbon dioxide was injected and circulated at a flow rate of 200 cc/min.

An analysis of the reaction product after conversion to acid form showed a para-hydroxybenzoic acid of 75.4% on the basis of potassium phenolate, with 1.6% salicylic acid forming as a by-product.

EXAMPLE 31

A pressure vessel was charged with 4.71 g of phenol, 17.56 g of potassium ortho-cresolate being in a dry powder form and 43 ml of NeoSK 1400 (a dibenzyltoluen mixture medium produced by Soken Chemical K.K.). With stirring, reaction was carried out at a carbon dioxide pressure of 3 kg/cm$^2$ (G) and at 270° C. for one hour. An analysis of the reaction mixture after conversion to acid form showed a para-hydroxybenzoic acid yield of 81.1% on the basis of phenol.

EXAMPLE 32

A pressure vessel was charged with 4.70 g of phenol, 25.57 g of potassium meta cresolate being in a dry powder form and 56 g of NeoSK 1400. With stirring, reaction was carried out at a carbon dioxide pressure of 9 kg/cm$^2$ (G) and at 320° C. for one hour. An analysis of the reaction mixture after conversion to acid form showed a para-hydroxybenzoic acid yield of 73.2% on the basis of phenol.

EXAMPLE 33

A pressure vessel was charged with 4.73 g of phenol, 23.52 g of potassium para cresolate being in a dry powder form and 54 ml of a high boiling point light oil fraction (160° to 230° C./10mmHg). Reaction was carried out at a carbon dioxide pressure of 4 kg/cm$^2$ (G) and at 250° C. for one hour. An analysis of the reaction mixture after conversion to acid form showed a para-hydroxybenzoic acid yield of 79.6% on the basis of phenol.

EXAMPLE 34

A pressure vessel was charged with 4.72 g of phenol, 24.10 g of potassium 3,5-xylenolate being in a dry powder form and 50 ml of NeoSK 1400. With stirring, reaction was carried out at a carbon dioxide pressure of 7 kg/cm$^2$ (G) and at 300° C. for one hour. An analysis of the reaction mixture after conversion to acid form showed a para-hydroxybenzoic acid yield of 83.8% on the basis of phenol.

EXAMPLE 35

A pressure vessel was charged with 4.71 g of phenol, 16.05 g of potassium 3,5-xylenolate being in a dry powder form and 38 g of NeoSK 1400. With stirring, reaction was carried out at a carbon dioxide pressure of 5 kg/cm$^2$ (G) and at 300° C. for one hour. An analysis of the reaction mixture after conversion to acid form showed a para-hydroxybenzoic acid yield of 78.4% on the basis of phenol.

EXAMPLE 36

A pressure vessel was charged with 4.70 g of phenol, 17.42 g of potassium 2,4,6-trimethylphenolate being in a dry powder form and 38 ml of NeoSK 1400. With stirring, reaction was carried out at a carbon dioxide pressure of 5 kg/cm$^2$ (G) and at 260° C. for 10 min. An analysis of the reaction mixture after conversion to acid form showed a para-hydroxybenzoic acid yield of 73.1% on the basis of phenol.

We claim:

1. A process for preparing unsubstituted para-hydroxybenzoic acid which comprises reacting unsubstituted potassium phenolate with carbon dioxide in an inert reaction medium or without using a reaction medium in the presence of at least one compound selected form the group consisting of the compounds represented by the following general formula I or II wherein compounds I and II are sources of potassium and are substantially free from carboxylation during said process:

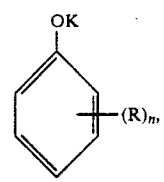

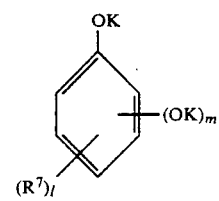

(in formula I, R may be any organic substituent with the proviso that it is not an aliphatic hydroxyl radical having up to 4 carbon atoms, an aliphatic mercapto radical having up to 4 carbon atoms, a substituent containing at least one of these radicals in its structural unit, and a hydrogen atom; in formula II, R' may be any organic substituent with the proviso that it is not an aliphatic hydroxyl radical having up to 4 carbon atoms, an aliphatic mercapto radical having up to 4 carbon atoms, and a substituent containing at least one of these radicals in its structural unit; in formula I, n is an integer of 1–5, provided that substituents R may be the same or different when n is 2 or more; and in formula II, m is an integer of 1–5 and l is an integer of 0–4, provided that substituents R' may be the same or different when l is 2 or more) at a reaction temperature of 230°–450° C., and at a carbon dioxide pressure ranging from atmospheric pressure to 6 kg/cm² (G).

2. A process for preparing para-hydroxybenzoic acid according to claim 1 wherein if at least either of (A) a mixed melting point of a mixture containing said potassium phenolate and at least one compound selected from the group consisting of the compounds represented by said general formula I or II and (B) the highest decarboxylation temperature of substituted potassium salicylates which are derived by ortho-carboxylation from a compound which is represented by said general formula I or II and has at least one hydrogen atom on the ortho position of the associated potassium oxy radical is within the range from 230° C. to 450° C., the reaction temperature is within the range from the higher temperature selected from said mixed melting point and said decarboxylation temperature to 450° C.

3. A process for preparing para-hydroxybenzoic acid according to claim 1 wherein said potassium phenolate and the compounds represented by said formula I or II are derived from tar acids and/or cresol acids.

4. A process for preparing para-hydroxybenzoic acid according to claim 1 wherein the reaction between potassium phenolate and carbon dioxide is performed in a flow or a circulation of carbon dioxide or carbon dioxide gas mixture containing product phenol, with part or all of the resulting compounds represented by the following general formula III or IV being recovered or not recovered from the reaction system:

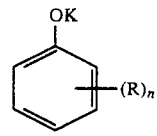

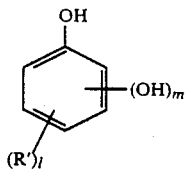

(in formula III, R and n are each the same as defined for formula I; and in formula IV, R', m and l are each the same as defined for formula II).

5. A process for preparing para-hydroxybenzoic acid according to claim 4 wherein if at least either of (A) a mixed melting point of a mixture containing said potassium phenolate and at least one compound selected from the group consisting of the compounds represented by said general formula I or II and (B) the highest decarboxylation temperature of substituted potassium salicylates which are derived by ortho-carboxylation from a compound which is represented by said general formula I or II and has at least one hydrogen atom on the ortho position of the associated potassium oxy radical is within the range from 230° C. to 450° C., the reaction temperature is within the range from the higher temperature selected from said mixed melting point and said decarboxylation temperature to 450° C.

6. A process for preparing para-hydroxybenzoic acid according to claim 4 wherein said potassium phenolate and the compounds represented by said formula I or II are derived from tar acids and/or cresol acids.

7. A process for producing unsubstituted para-hydroxybenzoic acid which comprises reacting unsubstituted potassium phenolate with carbon dioxide in an inert reaction medium or without using a reaction medium in the presence of at least one compound selected from the group consisting of the compounds represented by the following general formula I or II wherein compounds I and II are sources of potassium and are substantially free from carboxylation during said process:

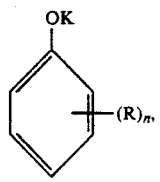

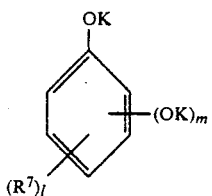

(in formula I, R may be any organic substituent with the proviso that it is not an aliphatic hydroxyl radical having up to 4 carbon atoms, an aliphatic mercapto radical having up to 4 carbon atoms, a substituent containing at least one of these radicals in its structural unit, and a hydrogen atom; in formula II, R' may be any organic substituent with the proviso that it is not an aliphatic hydroxyl radical having up to 4 carbon atoms, an aliphatic mercapto radical having up to 4 carbon atoms, and a substituent containing at least one of these radicals in its structural unit; in formula I, n is an integer of 1–5, provided that substituents R may be the same or different when n is 2 or more; and in formula II, m is an integer of 1–5 and l is an integer of 0–4, provided that substituents R' may be the same or different when l is 2 or more) at a reaction temperature of 230°–450° C. and at a carbon dioxide pressure ranging from atmospheric pressure to 6 kg/cm² (G), and further continuing the reaction with the pressure of carbon dioxide in the system being reduced and/or the reaction temperature being elevated within the range specified above.

8. A process for preparing para-hydroxybenzoic acid according to claim 7 wherein if at least either of (A) a mixed melting point of a mixture containing said potassium phenolate and at least one compound selected from the group consisting of the compounds represented by said general formula I or II and (B) the highest decarboxylation temperature of substituted potassium salicylates which are derived by ortho-carboxylation from a compound which is represented by said general formula I or II and has at least one hydrogen atom on the ortho position of the associated potassium oxy radical is within the range from 230° C. to 450° C., the reaction temperature is within the range from the higher temperature selected from said mixed melting point and said decarboxylation temperature to 450° C.

9. A process for preparing para-hydroxybenzoic acid according to claim 7 wherein said potassium phenolate and the compounds represented by said formulas I or II are derived from tar acids and/or cresol acids.

10. A process for preparing para-hydroxybenzoic acid according to claim 7 wherein the reaction between potassium phenolate and carbon dioxide is performed in a flow or a circulation of carbon dioxide or carbon dioxide gas mixture containing product phenol, with part or all of the resulting compounds represented by the following general formula III or IV being recovered or not recovered from the reaction system:

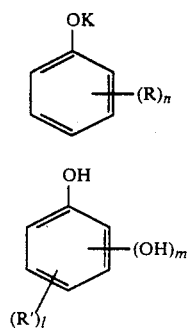

(in formula III, R and n are each the same as defined for formula I; and in formula IV, R', m and l are each the same as defined for formula II).

11. A process for preparing para-hydroxybenzoic acid according to claim 10 wherein if at least either of (A) a mixed melting point of a mixture containing said potassium phenolate and at least one compound selected from the group consisting of the compounds represented by said general formula I or II and (B) the highest decarboxylation temperature of substituted potassium salicylates which are derived by ortho-carboxylation from a compound which is represented by said general formula I or II and has at least one hydrogen atom on the ortho position of the associated potassium oxy radical is within the range from 230° C. to 450° C., the reaction temperature is within the range from the higher temperature selected from said mixed melting point and said decarboxylation temperature to 450° C.

12. A process for preparing para-hydroxybenzoic acid according to claim 10 wherein said potassium phenolate and the compounds represented by said formula I or II are derived from tar acids and/or cresol acids.

13. A process for preparing para-hydroxybenzoic acid according to claim 1 wherein the reaction between potassium phenolate and carbon dioxide is performed in a flow or a circulation of carbon dioxide or carbon dioxide gas mixture together with the addition of phenol, with part or all of the resulting compounds represented by the following general formula III or IV being recovered or not recovered from the reaction system:

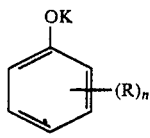

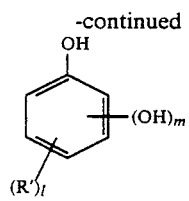

(in formula III, R and n are each the same as defined for formula I; and in formula IV, R', m and l are each the same as defined for formula II).

14. A process for preparing para-hydroxybenzoic acid according to claim 13 wherein if at least either of (A) a mixed melting point of a mixture containing said potassium phenolate and at least one compound selected from the group consisting of the compounds represented by said general formula I or II and (B) the highest decarboxylation temperature of substituted potassium salicylates which are derived by ortho-carboxylation from a compound which is represented by said general formula I or II and has at least one hydrogen atom on the ortho position of the associated potassium oxy radical is within the range from 230° C. to 450° C., the reaction temperature is within the range from the higher temperature selected from said mixed melting point and said decarboxylation temperature to 450° C.

15. A process for preparing para-hydroxybenzoic acid according to claim 13 wherein said potassium phenolate and the compounds represented by said formula I or II are derived from tar acids and/or cresol acids.

16. A process for preparing para-hydroxybenzoic acid according to claim 7 wherein the reaction between potassium phenolate and carbon dioxide is performed in a flow or a circulation of carbon dioxide or carbon dioxide gas mixture together with the addition of phenol, with part or all of the resulting compounds represented by the following general formula III or IV being recovered or not recovered from the reaction system:

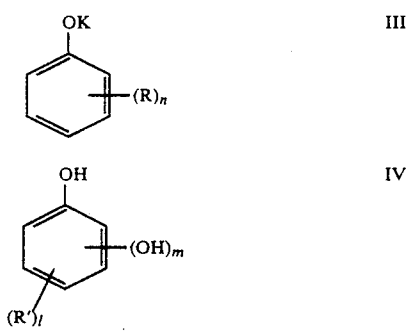

(in formula III, R and n are each the same as defined for formula I; and in formula IV, R', m and l are each the same as defined for formula II).

17. A process for preparing para-hydroxybenzoic acid according to claim 16 wherein if at least either of (A) a mixed melting point of a mixture containing said potassium phenolate and at least one compound selected from the group consisting of the compounds represented by said formula I or II and (B) the highest decarboxylation temperature of substituted potassium salicylates which are derived by orthocarboxylation from a compound which is represented by said formula I or II and has at least one hydrogen atom on the ortho position of the associated potassium oxy radical is within the range from 230° C. to 450° C., the reaction temperature is within the range from the higher temperature of said mixed melting point and said decarboxylation temperature to 450° C.

18. A process for preparing para-hydroxybenzoic acid according to claim 16 wherein said potassium phenolate and the compounds represented by said formula I or II are derived from tar acids and/or cresol acids.

19. A process for preparing unsubstituted para-hydroxybenzoic acid wherein the reaction of carbon dioxide and a mixture of unsubstituted phenol and at least one compound of the compounds represented by the following general formula I or II wherein compounds I and II are sources of potassium and are substantially free from carboxylation during said process is performed in an inert reaction medium or without using a reaction medium

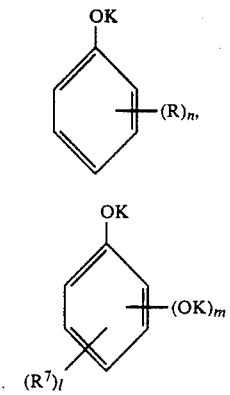

(in formula I, R may be an organic substituent with the proviso that it is not an aliphatic hydroxyl radical having up to 4 carbon atoms, an aliphatic mercapto radical having up to 4 carbon atoms, a substituent containing at least one of these radicals in its structural unit, and a hydrogen atom; in formula II, R' may be any organic substituent with the proviso that it is not an aliphatic hydroxyl radical having up to 4 carbon atoms, an aliphatic containing at least one of these radicals in its structural unit; in formula I, n is an integer of 1–5, provided that substituents R may be the same or different when n is 2 or more; and in formula II, m is an integer of 1–5 and l is an integer of 0–4, provided that substituents R' may be the same or different when l is 2 or more) at a reaction temperature of 230°–450° C. and at a carbon dioxide pressure ranging from atmospheric pressure to 6 kg/cm² (G).

20. A process for preparing para-hydroxybenzoic acid according to claim 19 wherein if at least either of (A) a melting point or a mixed melting point of at least one compound selected from the group consisting of the compounds represented by said general formula I or II and (B) the highest decarboxylation temperature of substituted potassium salicylates which are derived by ortho-carboxylation from a compound which is represented by said general formula I or II and has at least one hydrogen atom on the ortho position of the associated potassium oxy radical is within the range from 230° C. to 450° C., the reaction temperature is within the range from the higher temperature selected from said melting point or mixed melting point and said decarboxylation temperature to 450° C.

21. A process for preparing para-hydroxybenzoic acid according to claim 19 wherein said compounds represented by said formula I or II are derived from tar acids and/or cresol acids.

22. A process for preparing para-hydroxybenzoic acid according to claim 19 wherein the reaction among at least one compound selected from the group consisting of the compounds represented by said formula I or II, phenol and carbon dioxide is performed in a flow or a circulation of carbon dioxide or carbon dioxide gas mixture, with part or all of the resulting compounds represented by the following general formula III or IV being recovered or not recovered from the reaction system:

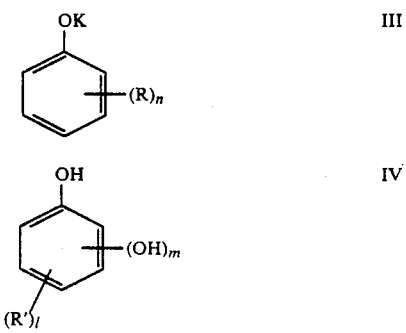

(in formula III, R and n are each the same as defined for formula I; and in formula IV, R', m and l are each the same as defined for formula II).

23. A process for preparing para-hydroxybenzoic acid according to claim 22 wherein the flow or the circulation of carbon dioxide or carbon dioxide gas mixture is preformed while phenol is added.

24. A process for preparing unsubstituted para-hydroxybenzoic acid wherein the reaction of carbon dioxide and a mixture of unsubstituted phenol and at least one compound of the compounds represented by the following general formula I or II wherein compounds I and II are sources of potassium and are substantially free from carboxylation during said process is performed in an inert reaction medium or without using a reaction medium;

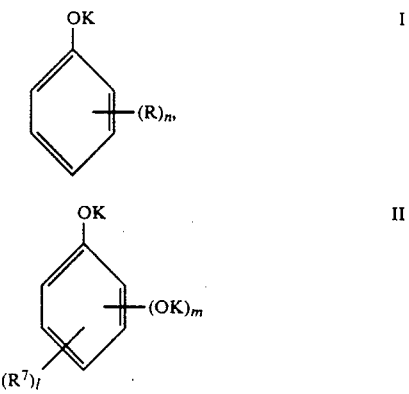

(in formula I, R may be any organic substituent with the proviso that it is not an aliphatic hydroxyl radical having up to 4 carbon atoms, an aliphatic mercapto radical having up to 4 carbon atoms, a substituent containing at least one of these radicals in its structural unit, and a hydrogen atom; in formula II, R' may be any organic substituent with the proviso that it is not an aliphatic hydroxyl radical having up to 4 carbon atoms, an aliphatic mercapto radical having up to 4 carbon atoms, and a substituent containing at least one of these radicals in its structural unit; in formula I, n is an integer of 1–5, provided that substituents R may be the same or different when n is 2 or more; and in formula II, m is an integer of 1–5 and l is an integer of 0–4, provided that substituents R' may be the same or different when l is 2 or more) at a reaction temperature of 230°–450° C. and at a carbon dioxide pressure ranging from atmospheric pressure to 6 kg/cm² (G), and further continuing the reaction with the pressure of carbon dioxide in the system being reduced and/or the reaction temperature being elevated within the range specified.

25. The process of claim 1, wherein R is a substitured or unsubstituted radical selected from the group consisting of alkyl, alkenyl, alkynyl, alkoxy, amino, imino, halogen, aromatic hydroxyl, nitro and phenyl and R' is a substituted or unsubstituted radical selected from the group consisting of alkyl, alkenyl, alkynyl, alkoxy, amino, imino, halogen, aromatic hydroxyl, nitro, phenyl, and hydrogen.

26. The process of claim 7, wherein R is a substituted or unsubstituted radical selected from the group consisting of alkyl, alkenyl, alkynyl, alkoxy, amino, imino, halogen, aromatic hydroxyl, nitro and phenyl and R' is a substituted or unsubstituted radical selected from the group consisting of alkyl, alkenyl, alkynyl, alkoxy, amino, imino, halogen, aromatic hydroxyl, nitro, phenyl, and hydrogen.

27. The process of claim 19, wherein R is a substituted or unsubstituted radical selected from the group consisting of alkyl, alkenyl, alkynyl, alkoxy, amino, imino, halogen, aromatic hydroxyl, nitro and phenyl and R' is a substituted or unsubstituted radical selected from the group consisting of alkyl, alkenyl, alkynyl, alkoxy, amino, imino, halogen, aromatic hydroxyl, nitro, phenyl, and hydrogen.

28. The process of claim 24, wherein R is a substituted or unsubstituted radical selected from the group consisting of alkyl, alkenyl, alkynyl, alkoxy, amino, imino, halogen, aromatic hydroxyl, nitro and phenyl and R' is a substituted or unsubstituted radical selected from the group consisting of alkyl, alkenyl, alkynyl, alkoxy, amino, imino, halogen, aromatic hydroxyl, nitro, phenyl, and hydrogen.

* * * * *

UNITED STATES PATENT AND TRADEMARK OFFICE
CERTIFICATE OF CORRECTION

PATENT NO.  : 5,124,477

DATED       : June 23, 1992

INVENTOR(S) : Toshinobu SUZUKI et al.

It is certified that error appears in the above-identified patent and that said Letters Patent is hereby corrected as shown below:

Item [57] Abstract:

Please change formula I from

" 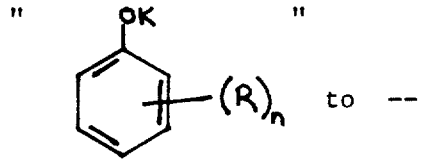 "   to --   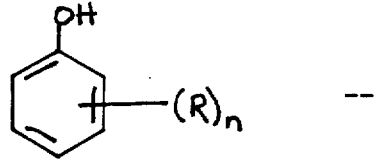   -- change formula II from

" 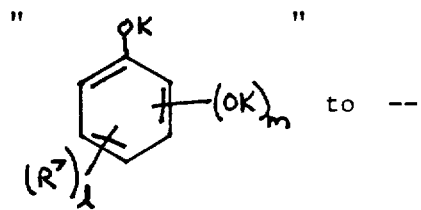 "   to --   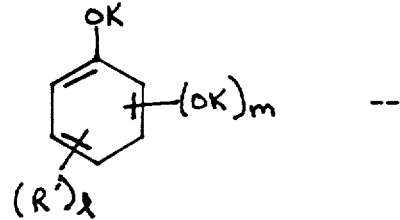   --

IN THE CLAIMS:
    Column 18,
    Claim 1 change formula II from

UNITED STATES PATENT AND TRADEMARK OFFICE
CERTIFICATE OF CORRECTION

PATENT NO. : 5,124,477

DATED : June 23, 1992

INVENTOR(S) : Toshinobu SUZUKI et al.

It is certified that error appears in the above-identified patent and that said Letters Patent is hereby corrected as shown below:

Col. 19,
 Claim 4 change formula III from

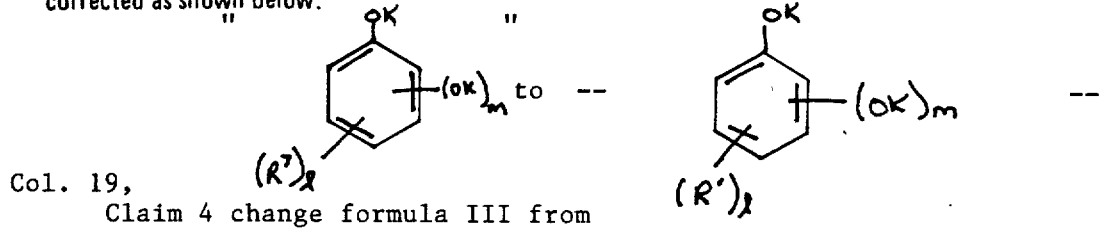

Col. 20,
 Claim 7 change formula II from

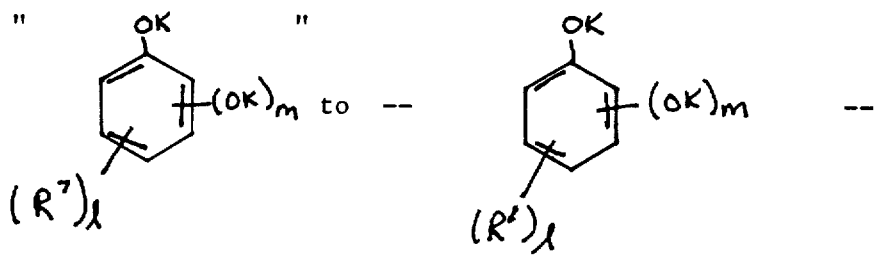

UNITED STATES PATENT AND TRADEMARK OFFICE
CERTIFICATE OF CORRECTION

PATENT NO. : 5,124,477
DATED : June 23, 1992
INVENTOR(S) : Toshinobu SUZUKI et al.

It is certified that error appears in the above-identified patent and that said Letters Patent is hereby corrected as shown below:

Col. 21,

Claim 10 change formula III from

" 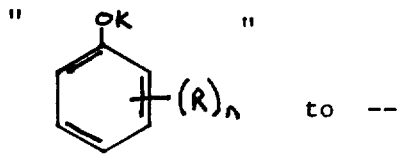 to -- 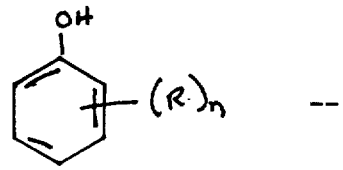 --

Col. 21,

Claim 13 change formula III from

" 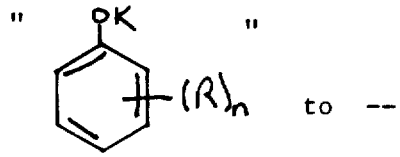 to -- 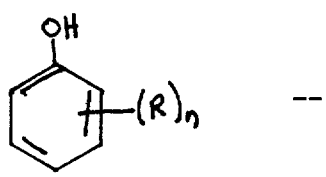 --

Col. 22,

Claim 16 change formula III from

UNITED STATES PATENT AND TRADEMARK OFFICE
CERTIFICATE OF CORRECTION

PATENT NO. : 5,124,477

DATED : June 23, 1992

INVENTOR(S) : Toshinobu SUZUKI et al.

It is certified that error appears in the above-identified patent and that said Letters Patent is hereby corrected as shown below:

Col. 23,

Claim 19 change formula II from 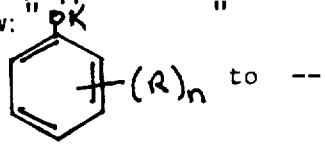 to -- 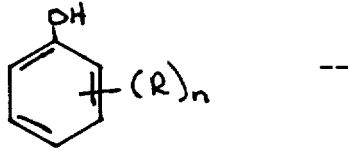 --

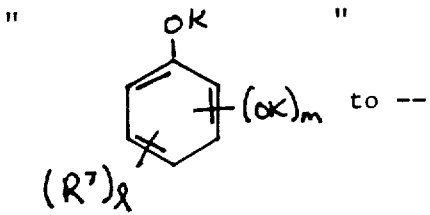 to -- 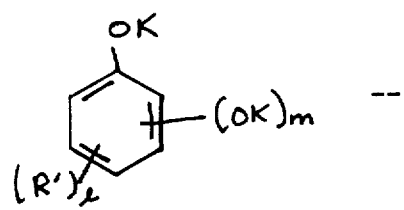 --

Claim 19, column 23, line 35, change "an" to --any--;

line 43, before "containing" insert --mercapto radical having up to 4 carbon atoms, and a substituent--.

Col. 24,

Claim 22 change formula III from

UNITED STATES PATENT AND TRADEMARK OFFICE
CERTIFICATE OF CORRECTION

PATENT NO. : 5,124,477

DATED : June 23, 1992

INVENTOR(S) : Toshinobu SUZUKI et al.

It is certified that error appears in the above-identified patent and that said Letters Patent is hereby corrected as shown below:

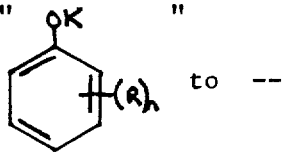 to -- 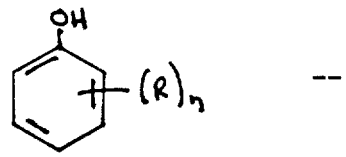 --

Col. 24,
  Claim 24 change formula II from

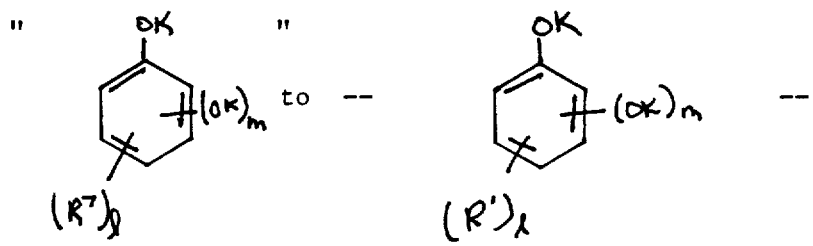

UNITED STATES PATENT AND TRADEMARK OFFICE
CERTIFICATE OF CORRECTION

PATENT NO. : 5,124,477
DATED : June 23, 1992
INVENTOR(S) : Toshinobu SUZUKI ET AL.

It is certified that error appears in the above-identified patent and that said Letters Patent is hereby corrected as shown below:

Column 3, change formula II from

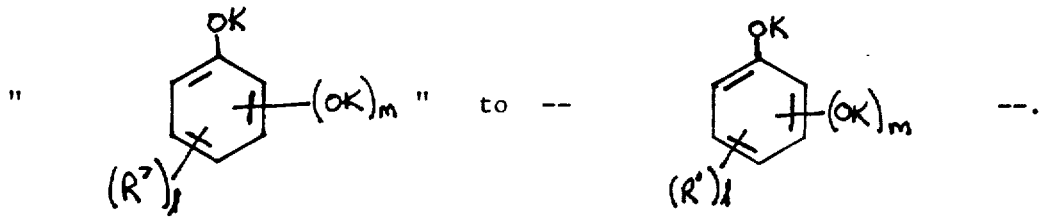

Column 4, change formula III from

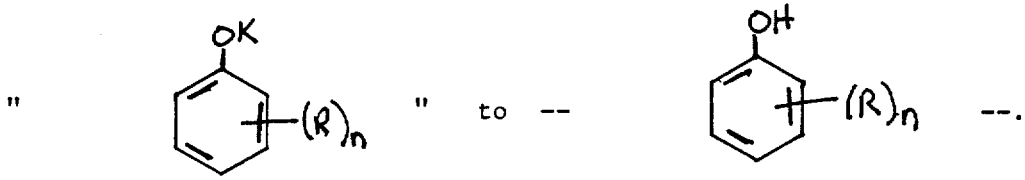

Column 5, change formula II from

UNITED STATES PATENT AND TRADEMARK OFFICE
CERTIFICATE OF CORRECTION

PATENT NO. : 5,124,477

DATED : June 23, 1992

INVENTOR(S) : Toshinobu SUZUKI ET AL.

It is certified that error appears in the above-identified patent and that said Letters Patent is hereby corrected as shown below:

Column 7, change formula III from " 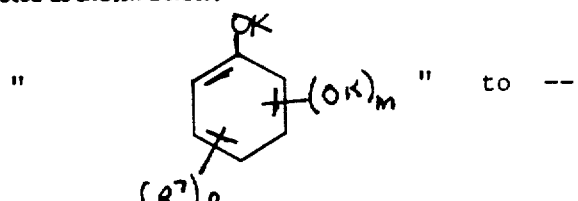 " to -- 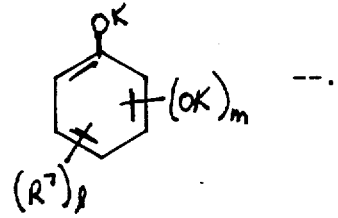 --.

" 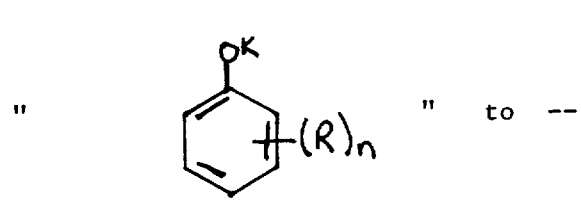 " to -- 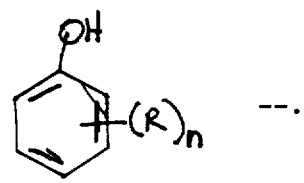 --.

Signed and Sealed this

Third Day of May, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,124,477
DATED : June 23, 1992
INVENTOR(S) : Toshinobu SUZUKI et al.

It is certified that error appears in the above-indentified patent and that said Letters Patent is hereby corrected as shown below:

Item [57] Abstract:

Please change formula I from

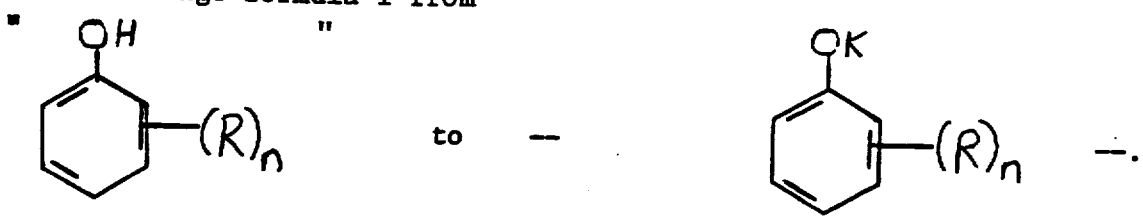

Column 5, change formula II from

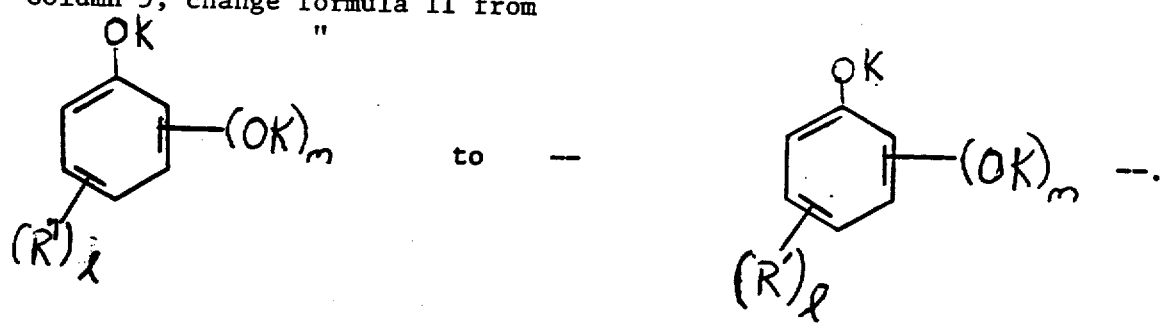

Signed and Sealed this

Seventh Day of February, 1995

BRUCE LEHMAN

Attest:

Attesting Officer                Commissioner of Patents and Trademarks